(12) United States Patent
Weinmann et al.

(10) Patent No.: US 6,566,413 B1
(45) Date of Patent: May 20, 2003

(54) POLYMERISABLE MATERIALS WHICH ARE BASED ON HARDENABLE SILOXANE COMPOUNDS

(75) Inventors: Wolfgang Weinmann, Gilching (DE); Joachim Zech, Seefeld (DE); Oswald Gasser, Seefeld (DE); Rainer Guggenberger, Herrsching (DE); Gunther Eckhardt, Bad Dürrenberg (DE); Peter Bissinger, Diessen (DE); Wolfgang Soglowek, Diessen-Obermühlhausen (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/868,525

(22) PCT Filed: Dec. 22, 1999

(86) PCT No.: PCT/EP99/10319

§ 371 (c)(1), (2), (4) Date: Sep. 19, 2001

(87) PCT Pub. No.: WO00/38619

PCT Pub. Date: Jul. 6, 2000

(30) Foreign Application Priority Data

Dec. 24, 1998 (DE) ......................... 198 60 364

(51) Int. Cl.⁷ ............................. C08F 2/46; A61K 6/00
(52) U.S. Cl. ................. 522/71; 522/148; 522/172; 522/99; 523/109; 523/115; 523/116; 523/118; 523/120; 433/180; 433/226; 433/228.1; 424/401; 528/32; 548/406
(58) Field of Search ................. 522/99, 71, 148, 522/172; 523/116, 115, 118, 120, 109; 433/226, 180, 228.1; 424/401; 528/32; 548/406

(56) References Cited

U.S. PATENT DOCUMENTS

| | | | |
|---|---|---|---|
| 3,726,943 A | | 4/1973 | Joy |
| 4,877,854 A | * | 10/1989 | Hattori et al. ............... 523/107 |
| 5,064,891 A | * | 11/1991 | Fujiki et al. ................ 523/109 |
| 5,371,162 A | * | 12/1994 | Konings et al. ............ 524/188 |
| 5,468,477 A | * | 11/1995 | Kumar et al. ................ 424/49 |
| 6,335,413 B1 | * | 1/2002 | Zech et al. .......... 424/DIG. 16 |

FOREIGN PATENT DOCUMENTS

| | | |
|---|---|---|
| DE | 3741575 | 6/1990 |

(List continued on next page.)

Primary Examiner—James J. Seidleck
Assistant Examiner—Sanza L. McClendon
(74) Attorney, Agent, or Firm—Birch, Stewart, Kolasch & Birch, LLP

(57) ABSTRACT

The invention relates to novel cyclic siloxane compounds of the following general formula (I):

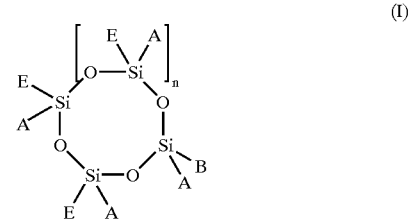

in which:
n=0, 1, 2, 3, 4, 5, 6, 7, 8, 9, 10 preferably 1, 2, 3, 4, 5;
A=H or $C_1$–$C_{15}$ alk(en)yl, $C_3$–$C_{15}$ cycloalk(en)yl, $C_6$–$C_{12}$ aryl, $C_8$–$C_{18}$ alkaryl, where, in the said radicals, in each case one or more C atoms can be replaced by O, C=O, O(C=O), $SiR_2$ and/or NR, R being an aliphatic radical with 1 to 7 C atoms, in which one or more C atoms can be replaced by O, C=O, and/or O(C=O);
B=E or a linear, branched or polycyclic aliphatic- or aromatic-groups-containing hydrocarbon radical which links 2 to 10 of the cyclosiloxane radicals defined above, less B, to one another and contains 2 to 50 C atoms and additionally 0 to 30 other atoms from the group O, N, S, P, Si, Cl, F, Br, I and from which correspondingly 1 to 9, preferably 1 to 4 of the above defined cyclosiloxane radicals, less B, are pending;
E=A or a polymerizable group G—Q—L, where on average up to 50% or less of the groups E correspond to representatives of A;
G=$C_{1-10}$ alk(en)ylene;
Q=O, N—A or a di- or polyvalent linear, branched or cyclic alcohol, amine or aminoalcohol radical with 2 to 10 C atoms;
L=an organic radical, containing a C=C double bond, with 2 to 10 C atoms;
and with the proviso that no annelated siloxane ring systems can occur in (I),
and also dental compositions which contain the compounds of formula (I) and/or compounds of formula (II):

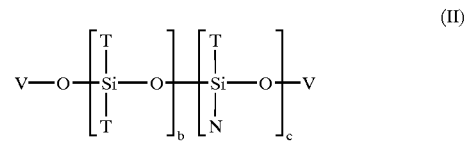

in which:
T=independently of each other H or $C_1$–$C_{10}$ alk(en)yl, $C_3$–$C_{10}$ cycloalk(en)yl, $C_6$–$C_{12}$ aryl or $C_8$–$C_8$ alkaryl;
N=a polymerizable group $R^1$—$R^2$—$R^3$;
b=0 to 500, where the proportion b may be at most 50% of the repeat units (b+c);
c=1 to 1000;
$R^1$=$C_1$–$C_{10}$ alk(en)ylene;
$R^2$=O, N—T or a di- or polyvalent linear, branched or cyclic alcohol, amine or aminoalcohol radical with 2 to 10 C atoms;
$R^3$=an organic radical, containing a C=C double bond, with 3 to 10 C atoms;
V=$SiMe_2T$, $SiEt_2T$, $SiMePhT$, $SiPh_2T$.

7 Claims, No Drawings

FOREIGN PATENT DOCUMENTS

| | | | |
|---|---|---|---|
| DE | 19525468 | 1/1997 | |
| DE | 19648283 A1 * | 5/1998 | ............ A61K/6/08 |
| DE | 19736665 * | 2/1999 | .......... A61K/6/083 |
| EP | 2261520 | 3/1988 | |
| EP | 2369394 | 5/1990 | |
| EP | 0398745 A2 * | 11/1990 | ........... C08L/83/07 |
| EP | 2866086 | 9/1998 | |
| FR | 9815715 | 6/2000 | |
| GB | 897973 | 6/1962 | |
| GB | 2023628 | 1/1980 | |
| GB | 2086914 A * | 5/1982 | ......... C08F/220/04 |
| WO | WO 9600560 A2 * | 1/1996 | ............ A61K/6/10 |
| WO | WO 9822521 A1 * | 5/1998 | ........... C08G/59/02 |

* cited by examiner

POLYMERISABLE MATERIALS WHICH ARE BASED ON HARDENABLE SILOXANE COMPOUNDS

This application is the national phase under 35 U.S.C. §371 of PCT International Application No. PCT/EP99/10319 which has an International filing date of Dec. 22, 1999, which designated the United States of America and was not published in English.

The present invention relates to polymerizable compositions, based on curable siloxane compounds, for dental and dental engineering applications.

Hitherto predominantly ethylenically unsaturated monomers, preferably methacrylate and acrylate monomers, have been used in polymerizable dental compositions.

The 2,2-bis[4,1-phenyleneoxy(2-hydroxy-3,1-propanediyl)-methacrylic acid ester]-propylidene (bis-GMA) described by Bowen [U.S. Pat. No. 3,066,112] is used particularly frequently. Mixtures of this methacrylate with triethylene glycol dimethacrylate (TEGDMA) still serve even today as the standard formulation for dental plastic direct filling materials. Methacryl derivatives of the double-formylated bis-(hydroxymethyl)tricyclo[$5.2.1.0^{2,6}$] decane have also proved themselves as monomers for dental composites [W. Gruber at al., DE-A-27 14 538; W. Schmitt et al., DE-C-28 16 823; J. Reiners et al., EP-A-0 261 520].

Common to all these compositions is the disadvantageous polymerization shrinkage occurring during polymerization. This can lead for example in the application as filling material to the formation of discolorations at the cavity edge of the tooth or even to the development of edge cracks with subsequent risk of secondary caries.

Attempts have therefore been made in the past to reduce the polymerization shrinkage of the dental compositions through as great as possible a proportion of inorganic fillers. However, this normally leads to a clear increase in the viscosity of such compositions with handling drawbacks for the user, who must then have recourse where necessary to auxiliary means such as e.g. ultrasound for the processing of these materials [EP-0-480 472].

Customarily used dental monomers in most cases contain one or at most two polymerizable groups. A higher functionality for radically crosslinking groups per molecule leads as a rule to very highly viscous substances which can be mixed with filler only with difficulty and lead to very brittle materials in the cured state.

However, low-functionalized monomers have the disadvantage that they provide few linkage points for crosslinking and are therefore still present as monomers even after the curing reaction if the polymerization of all the monomers is not complete (which is practically never 100% achieved). These so-called residual monomers can be dissolved out of the dental material over an extended period of time and lead to unwanted side-effects in the organism.

The object of the present invention was therefore to provide monomers for dental compositions which, despite a high density of groups capable of polymerization, display a low viscosity, permit a high filler uptake and lead to compositions with a low polymerization shrinkage.

The object was achieved by the provision of novel monomers of the following general formula (I):

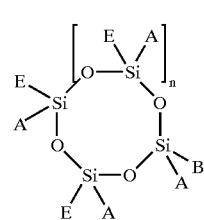

in which:
n=0, 1, 2, 3, 4, 5, 6, 7, 8, 9, 10 preferably 1, 2, 3, 4, 5;

A=H or $C_1$–$C_{15}$ alk(en)yl, preferably methyl, ethyl, propyl, butyl, vinyl, ethinyl, allyl, $C_3$–$C_{15}$ cycloalk(en)yl, preferably cyclopentyl, cyclohexyl, cyclopentadienyl, cyclohexenyl, $C_6$–$C_{12}$ aryl, preferably phenyl, tolyl, xylyl, $C_8$–$C_{18}$ alkaryl, preferably phenylethylenyl, where, in the said radicals, in each case one or more C atoms can be replaced by O, C=O, O(C=O), $SiR_2$ and/or NR, R being an aliphatic radical with 1 to 7 C atoms, in which one or more C atoms can be replaced by O, C=O, and/or O(C=O);

B=E or a linear, branched or polycyclic aliphatic- or aromatic-groups-containing hydrocarbon radical which links 2 to 10, preferably 2 to 5 cyclosiloxane radicals defined above, less B, to one another and contains 2 to 50, preferably 2 to 30 C atoms and additionally 0 to 30, preferably 0 to 20 other atoms from the group O, N, S, P, Si, Cl, F, Br, I and from which correspondingly 1 to 9, preferably 1 to 4 of the above defined cyclosiloxane radicals, less B, are pending; particularly preferred radicals B are: di(prop-3-yl)ether, di(prop-3-yl)sulfide, di(prop-3-yl)amine, di(prop-3-yl)-methyl-amine, tri(prop-3-yl)amine, di(prop-3-yl)urea, di(prop-3-yl)carbonate, ethylene glycol di(prop-3-yl)carbonate, diethylene glycol di(prop-3-yl)carbonate, ethylene glycol di(prop-3-yl)ether, diethylene glycol di(prop-3-yl)ether, 1,2-propanediol di(prop-3-yl)ether, 1,3-propanediol di(prop-3-yl)ether, 1,3-butanediol di(prop-3-yl)ether, 1,4-butanediol di(prop-3-yl)ether, 1,4-butenediol di(prop-3-yl)ether, 1,4-butinediol di(prop-3-yl)ether, 1,5-pentanediol di(prop-3-yl)ether, 16-hexanediol di(prop-3-yl)ether, 1,8-octanediol di(prop-3-yl)ether, 1,9-nonanediol di(prop-3-yl)ether, 1,10-decanediol di(prop-3-yl)ether, 1,12-dodecanediol di(prop-3-yl)ether, oxalic acid di(prop-3-yl)ester, malonic acid-di(prop-3-yl)ester, succinic acid di(prop-3-yl)ester, adipic acid di(prop-3-yl)ester, sebacic acid di(prop-3-yl)ester, 1,2-ethanediyl, 1,4-pentadienyl, 1,5-pentanediyl, 1,5-hexadienyl, 1,6-heptadienyl, 1,7-octadienyl, 1,8-nonadienyl, 1,9-decadienyl, 1,11-dodecadienyl, p-di(eth-2-yl)benzene, bis-4-(prop-3-yl)oxyphenyl)-sulfone, bis-4-(prop-3-yl)oxyphenyl)-ketone, bis-4-(prop-3-yl)-oxyphenyl)methane, 1,1-bis-(4-(prop-3-yl)oxyphenyl)-ethane, 2,2-bis-(4-(prop-3-yl)oxyphenyl)-propane, 2,2-bis-(4-(prop-3-yl)oxyphenyl)-perfluoropropane, 2,2-bis-(4-(prop-3-yl)oxy-3,5-dibromo-phenyl)-propane, 3,3-bis-(4-(prop-3-yl)-oxyphenylpentane, 4,4-bis-(4-(prop-3-yl)oxyphenyl)-heptane, 1,1-bis-(4-(prop-3-yl)oxyphenyl)-cyclopentane, 1,1-bis-(4-(prop-3-yl)-oxyphenyl)-cyclohexane, 1,1-bis-(4-(prop-3-yl)oxyphenyl)-3,3,5-trimethylcyclohexane, 1,1,1-tris-(4-(prop-3-yl)oxyphenyl)-ethane, bis-((prop-3-yl-ether)oxy)-tricyclo[$5.2.1.0^{2,6}$]decane:

E=A or a polymerizable group G—Q—L, where on average up to 50%, preferably 25% or less of the groups E correspond to representatives of A;

G=C$_{1-10}$ alk(en)ylene, preferably ethylene, methylethylene, propylene, butylene, hexylene, ethenylene, propenylene;

Q=O, N—A or a di- or polyvalent linear, branched or cyclic alcohol, amine or aminoalcohol radical with 2 to 10 C atoms, preferably ethanediol-diyl, glycerol-triyl, trimethylolpropane-triyl, pentaerythritol-tetryl;

L=an organic radical, containing a C═C double bond, with 2 to 10 C atoms, preferably acryl or methacryl.

Compounds according to formula (I) are cyclic siloxanes, in which one or more siloxane rings can occur per molecule. However, compounds in which annelated siloxane ring systems are present are expressly excluded.

The preparation of compounds of the general formula (I) takes place by suitable methods.

Si—H-functional cyclosiloxanes can be linked to C—C-unsaturated organic structures by hydrosilylation in particular (B. Marciniec: Comprehensive Handbook on Hydrosilylation, Pergamon Press, 1992). The properties of both monomers and polymers can be set in desired manner in this way.

For example, 1,3,5,7-tetramethylcyclotetrasiloxane can be linked to a representative of (I) in a solvent, such as toluene, under the influence of precious-metal catalysts, such as Speir catalysts or else Wilkinson catalysts, with four mol allyl methacrylate. Instead of the cyclotetrasiloxane, a commercially available SiH cycle mixture (a mixture of (SiMeHO)$_n$ with n preferably 4, 5, 6) can also be used. Instead of allyl methacrylate, other allyl ethers, esters or amides of (meth)acryl-functional organic molecules can be used.

In the case of the reaction of polyfunctional SiH-cyclosiloxanes with likewise multiple C—C unsaturated organic structures, all C—C unsaturated functions of the organic structure can be saturated with in each case a cyclosiloxane ring through a suitable reaction procedure. However, pre-crosslinked intermediate products can also be produced by a different choice of stoichiometry or reaction procedure.

Both possibilities are meant here.

These SiH-functional preliminary stages can for example be reacted with allyl methacrylate to produce further representatives of (I).

The particularly preferred structures shown in the following are as a rule obtained by hydrosilylation of allyl or vinyl compounds with SiH-containing compounds. With such a hydrosilylation reaction, for example of an allyl group with Si—H, n-propylene (β-adduct) and methylethylene bridges (α-adduct) occur to a varying extent, depending on whether the Si—H function is added against or according to Markovnikov's rule. The particularly preferred structures listed below show only the n-propylene (β-adduct) adducts in the structural formula. However, all possible mixtures of α- and β-adducts which always occur in the mixture during the reaction are meant (see following diagram).

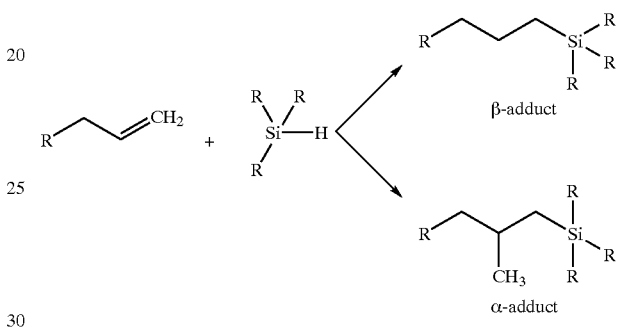

It was surprisingly found that these compounds, despite their high density of acrylate or methacrylate groups, display a very low viscosity and are outstandingly suitable for use in dental compositions.

Particularly preferred representatives of the compounds according to the general formula (I) are:

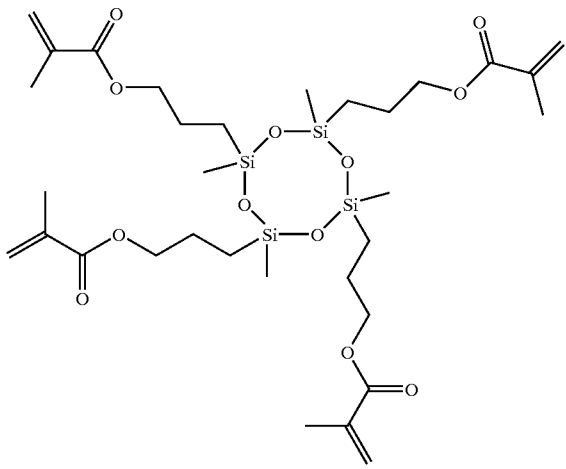

n =1, A = methyl, B = E, G = 1,3-propanediyl, Q = O, L = methacryl

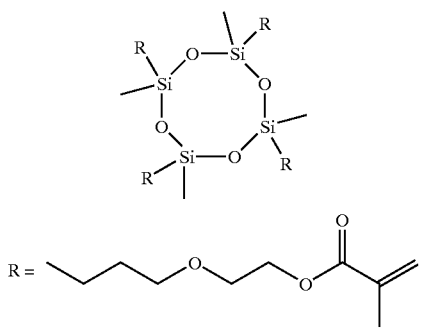

n = 1, A = methyl, B = E, G = 1,3-propanediyl, Q = ethanediol-diyl, L = methacryl -continued
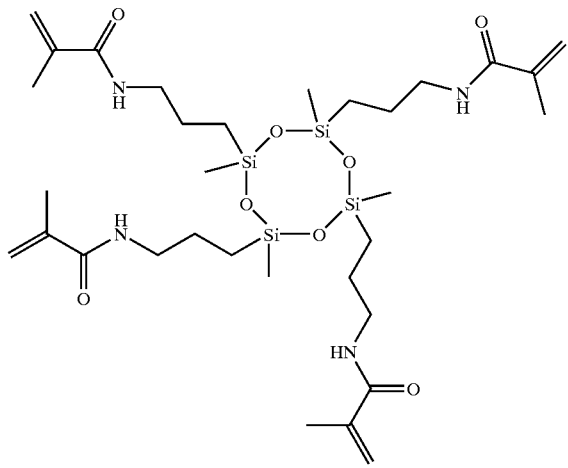
n = 1, A = methyl (at Si) or H (at N), B = E, G = 1,3-propanediyl, Q = N, L = methacryl
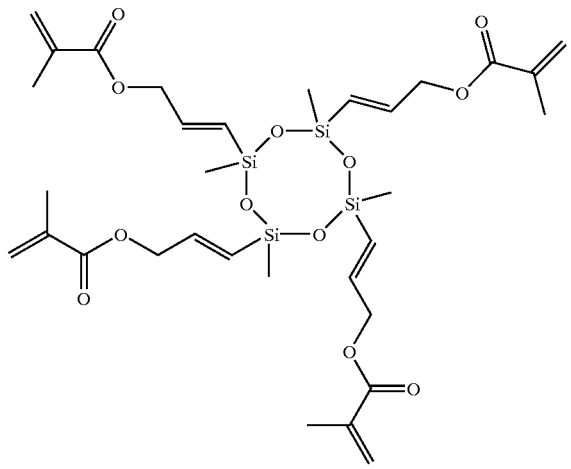
n = 1, A = methyl, B = E, G = 1,3-propanediyl, Q = O, L = methacryl
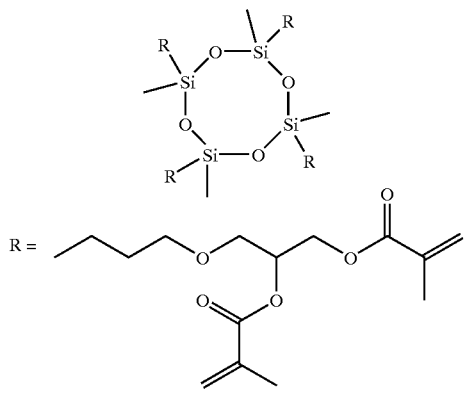
n = 1, A = methyl, B = E, G = 1,3-propanediyl, Q = glycerol-triyl, L = methacryl
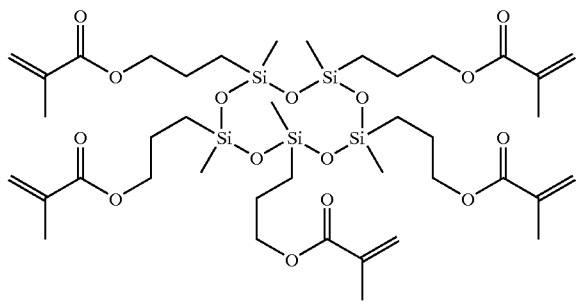
n = 2, A = methyl, B = E, G = 1,3-propanediyl, Q = O, L = methyacryl
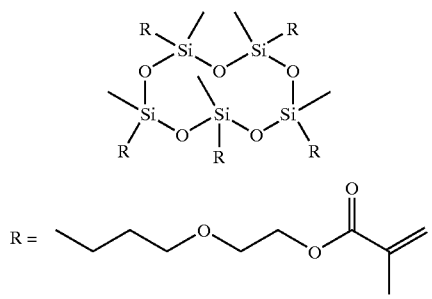
n = 2, A = methyl, B = E, G = 1,3-propanediyl, Q = ethanediol-diyl, L = methacryl
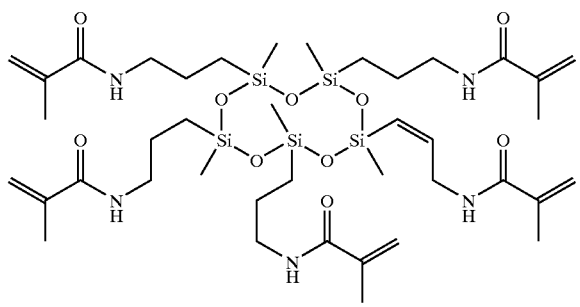
n = 2, A = methyl (at Si) or H (at N), B = E, G = 1,3-propanediyl, Q = N, L = methacryl -continued

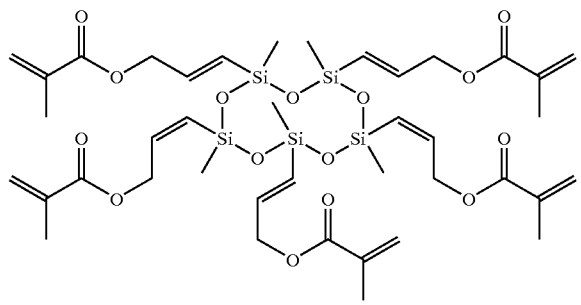

n = 2, A = methyl, B = E, G = 1,3-propanediyl, Q = O, L = methacryl

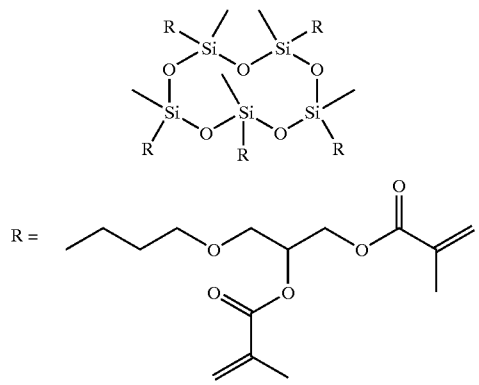

n = 2, A = methyl, B = E, G = 1,3-propanediyl, Q = ethanediol-diyl, L = methacryl

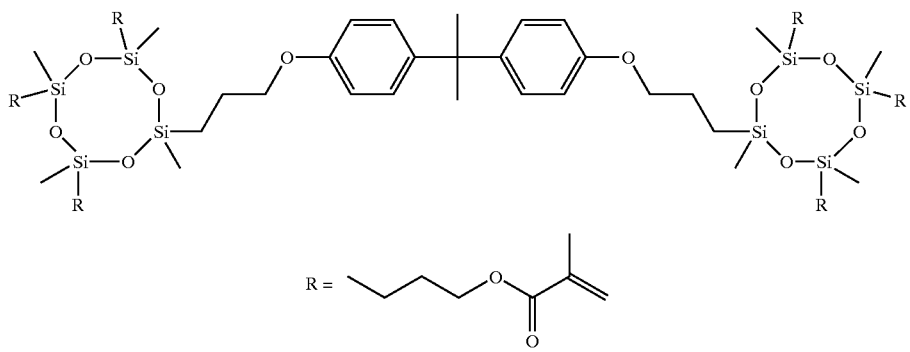

n = 1, A = methyl, B = 2,2-bis-(4-hydroxyphenyl)propane-diyl, G = 1,3- propanediyl, Q = O, L = methacryl

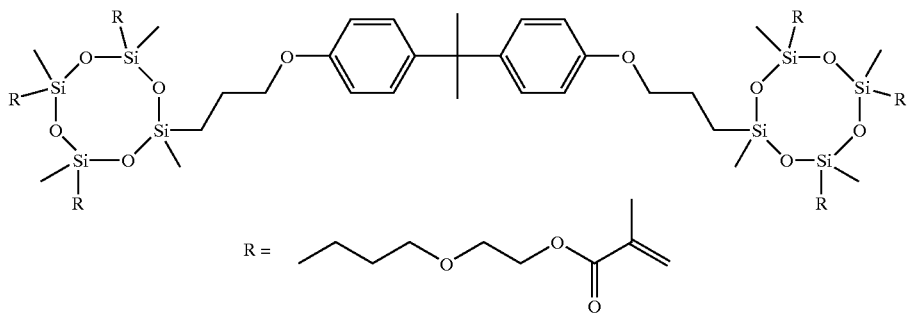

n = 1, A = methyl, B = 2,2-bis-(4-hydroxyphenyl)propane-diyl, G = 1,3- propanediyl, Q = ethanediol-diyl, L = methacryl

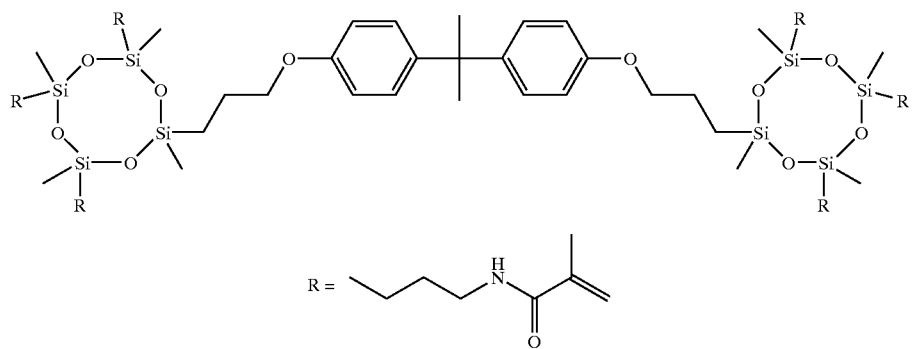

n = 1, A = methyl (at Si) or H (at N), B = 2,2-bis-(4-hydroxyphenyl)propane-diyl, G = 1,3-propanediyl, Q = N, L = methacryl

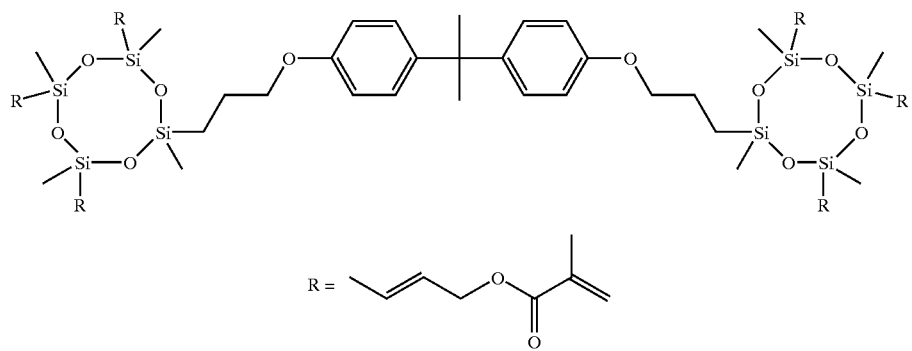

n = 1, A = methyl, B = 2,2-bis-(4-hydroxyphenyl)propane-diyl, G = 1,3-propanediyl, Q = O, L = methacryl

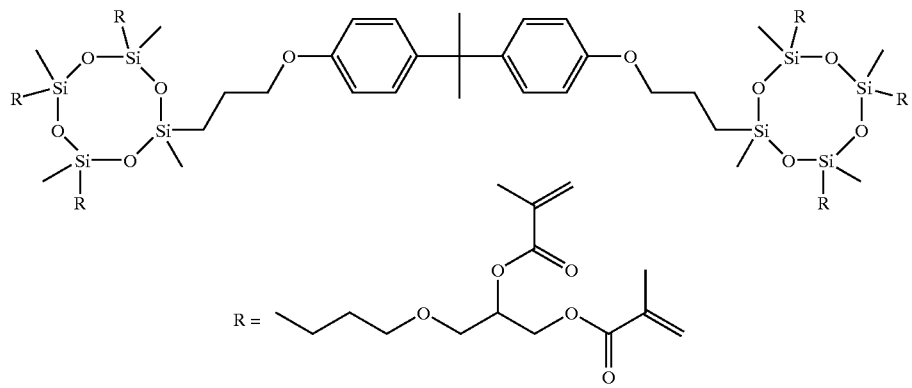

n = 1, A = methyl, B = 2,2-bis-(4-hydroxyphenyl)propane-diyl, G = 1,3-propanediyl, Q = glycerol-triyl, L = methacryl

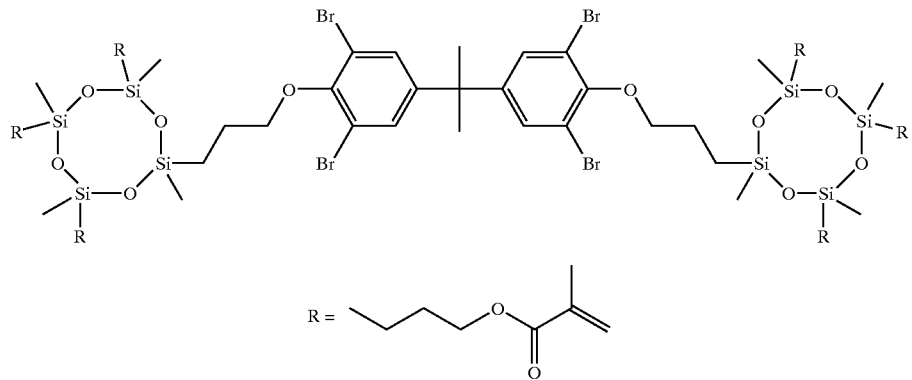

n = 1, A = methyl, B = 2,2-bis-(4-hydroxy-3,5-dibromophenyl)propane-diyl, G = 1,3-propanediyl, Q = O, L = methacryl

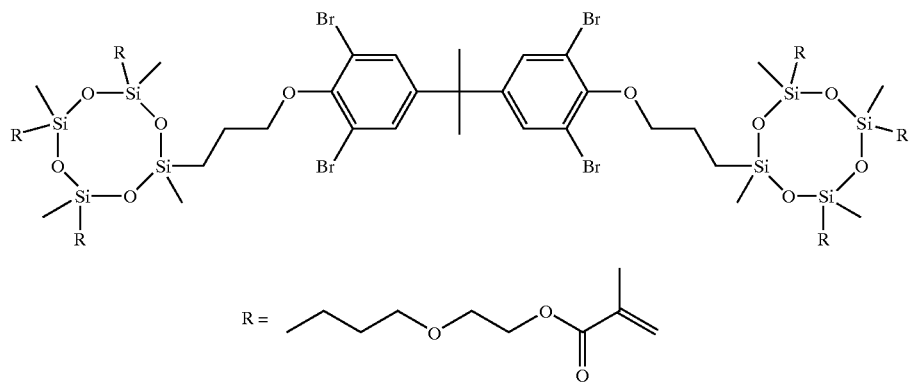

n = 1, A = methyl, B = 2,2-bis-(4-hydroxy-3,5-dibromophenyl)propane-di yl,G = 1,3-propanediyl, Q = ethanediol-diyl, L = methacryl -continued
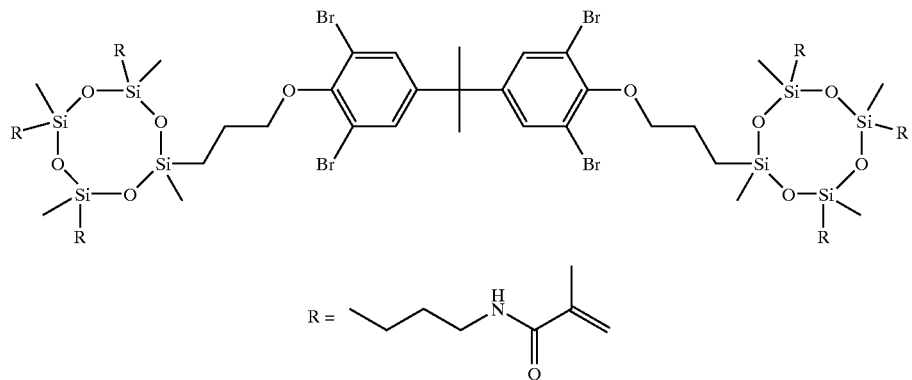
n = 1, A = methyl (at Si) or H (at N), B = 2,2-bis-(4-hydroxy-3,5-dibromophenyl)-propane-diyl, G = 1,3-propanediyl, Q = N, L = methacryl
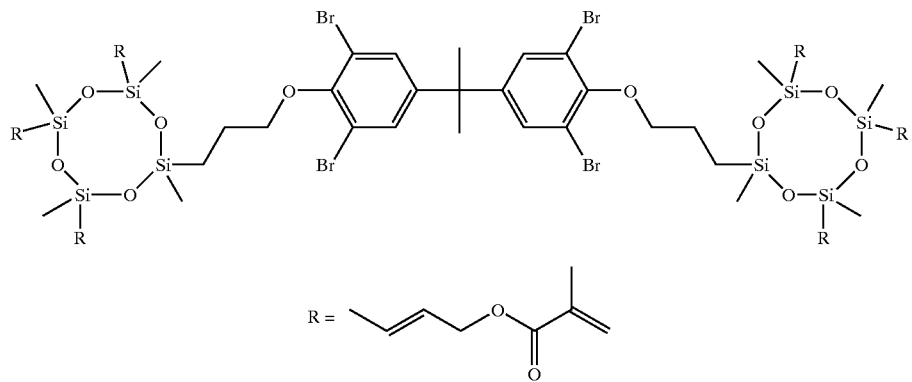
n = 1, A = methyl, B = 2,2-bis-(4-hydroxy-3,5-dibromophenyl)-propane-diyl, G = 1,3-propanediyl, Q = O, L = methacryl
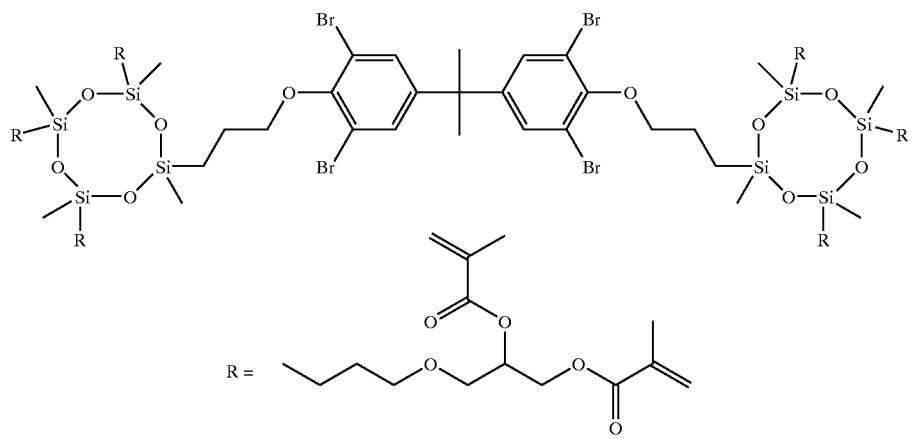
n = 1, A = methyl, B = 2,2-bis-(4-hydroxy-3,5-dibromophenyl)propane-diyl, G = 1,3-propanediyl, Q = glycerol-triyl, L = methacryl -continued
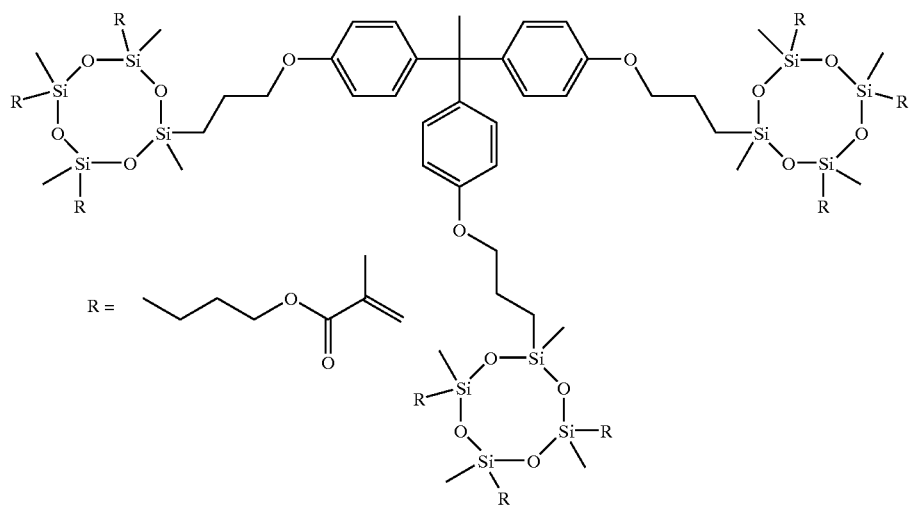
n = 1, A = methyl, B = 1,1,1-tris-(4-(prop-3-yl)oxyphenyl)-ethane-tr iyl, G = 1,3-propanediyl, Q = O, L = methacryl
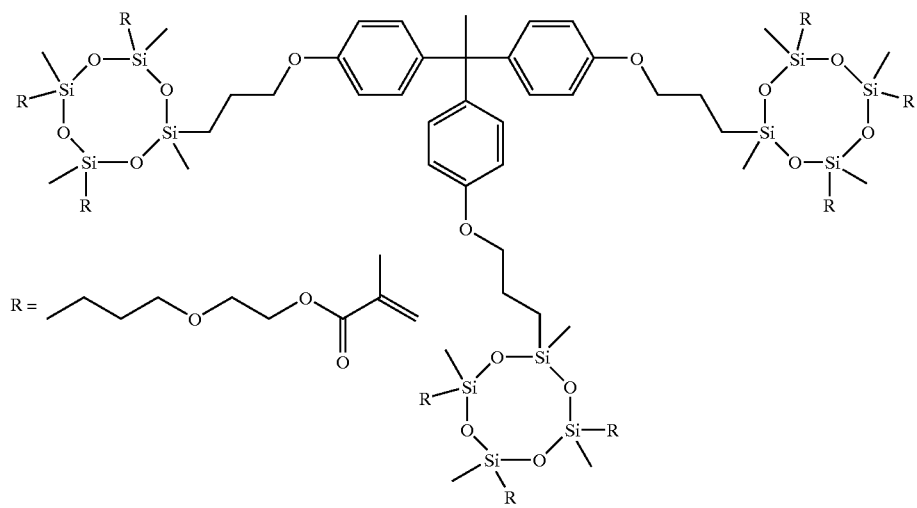
n = 1, A = methyl, B = 1,1,1-tris-(4-(prop-3-yl)oxyphenyl)-ethane-tr iyl, G = 1,3-propanediyl, Q = ethanediol-diyl, L = methacryl
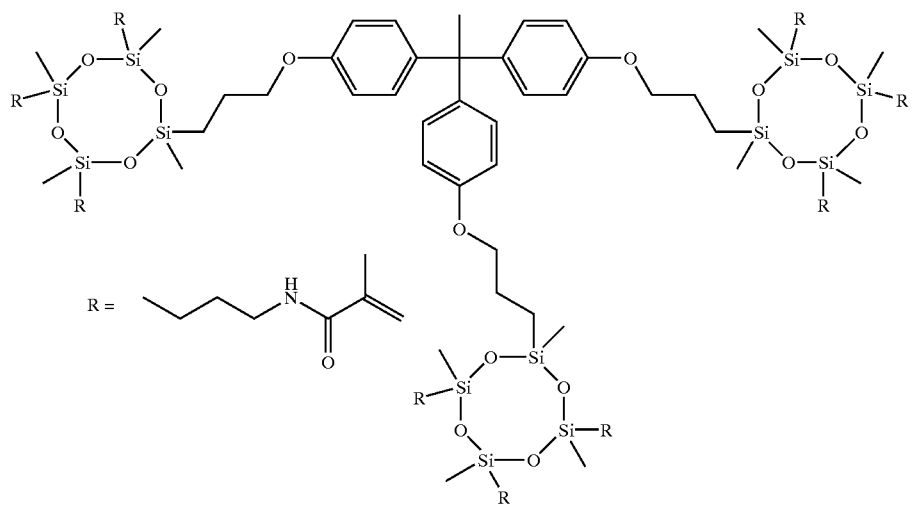
n = 1, A = methyl, B = 1,1,1-tris-(4-(prop-3-yl)oxyphenyl)-ethane-tr iyl, G = 1,3-propanediyl, Q = NH, L = methacryl

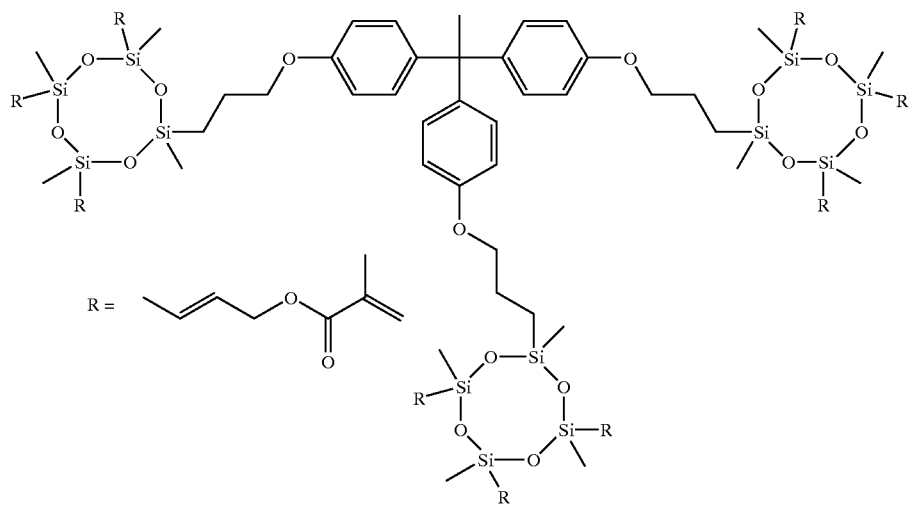
n = 1, A = methyl, B = 1,1,1-tris-(4-(prop-3-yl)oxyphenyl)-ethane-tr iyl, G = 1,3-propanediyl, Q = O, L = methacryl
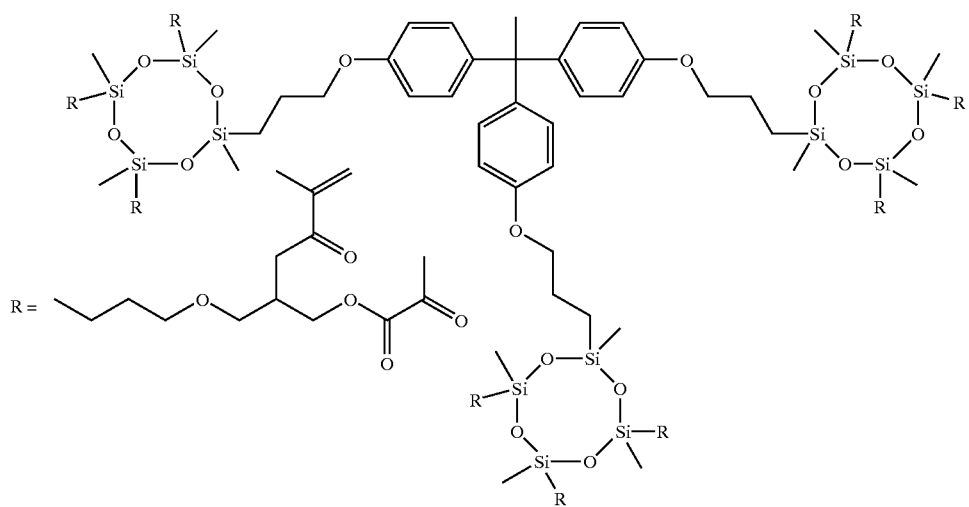
n = 1, A = methyl, B = 1,1,1-tris-(4-(prop-3-yl)oxyphenyl)-ethane-tr iyl, G = 1,3-propanediyl, Q = glycerol-triyl, L = methacryl
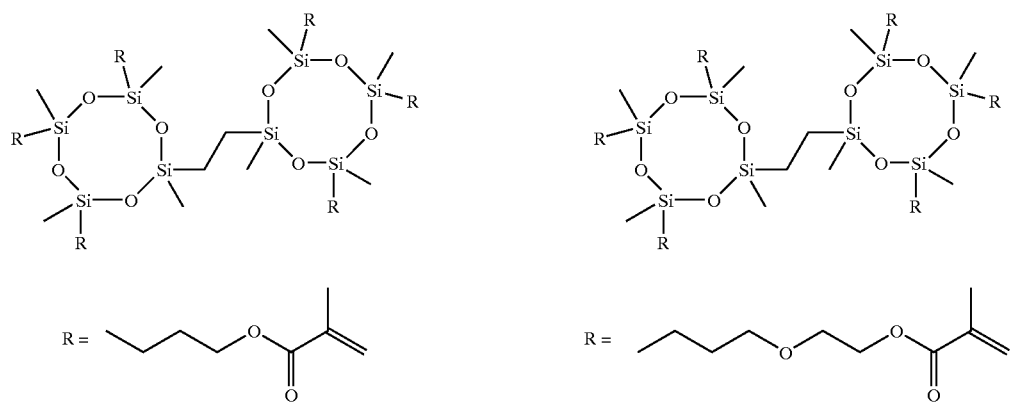
n = 1, A = methyl, B = 1,2-ethanediyl, G = 1,3-propanediyl, Q = O, L = methacryl
n = 1, A = methyl, B = 1,2-ethanediyl, G = 1,3-propanediyl, Q = ethanediol-diyl, L = methacryl -continued

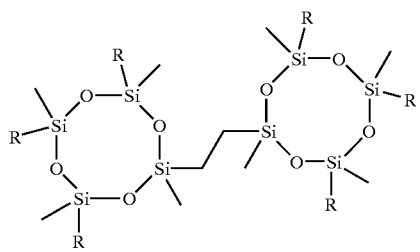

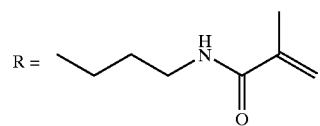

n = 1, A = methyl (at Si) or H (at N), B = 1,2-ethanediyl, G = 1,3-propanediyl, Q = N, L = methacryl

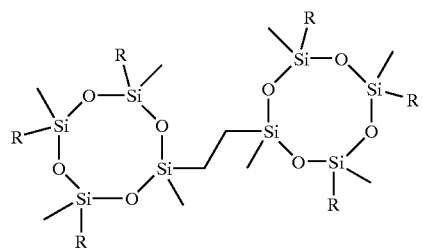

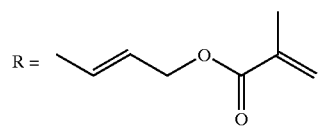

n = 1, A = methyl, B = 1,2-ethanediyl, G = 1,3-propanediyl, Q = O, L = methacryl

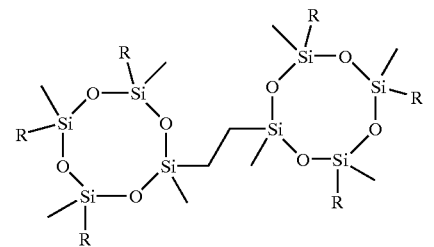

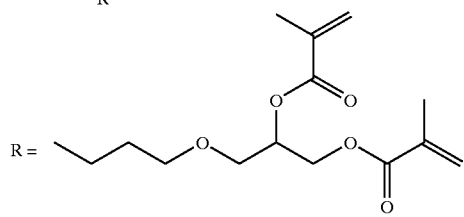

n = 1, A = methyl, B = 1,2-ethanediyl, G = 1,3-propanediyl, Q = glycerol-triyl, L = methacryl

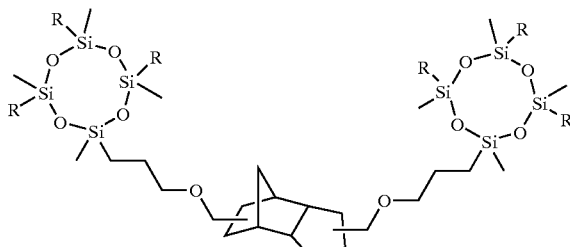

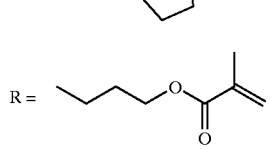

n = 1, A = methyl, B = tricyclo[5.2.1.0$^{2,6}$]decane-diyl, G = 1,3-propanediyl, Q = O, L = methacryl.

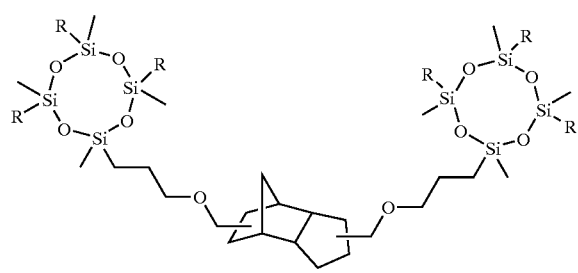

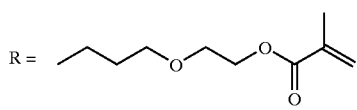

n = 1, A = methyl, B = tricyclo[5.2.1.0$^{2,6}$]decane-diyl, G = 1,3-propanediyl, Q = ethanediol-diyl, L = methacryl.

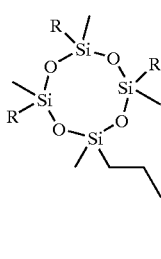

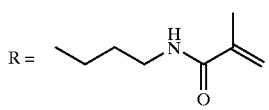

n = 1, A = methyl(at Si) or H(at N), B = tricyclo[5.2.1.0$^{2,6}$]decane-diyl, G = 1,3-propanediyl, Q = N, L = methacryl.

-continued

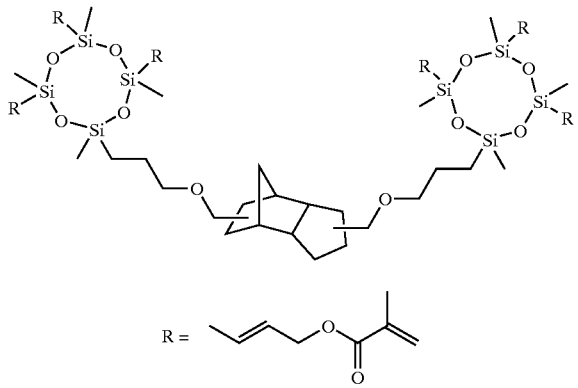

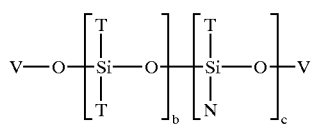

n = 1, A = methyl, B = tricyclo[5.2.1.0$^{2,6}$]decane-diyl, G = 1,3-propanediyl,
Q = O, L = methacryl.

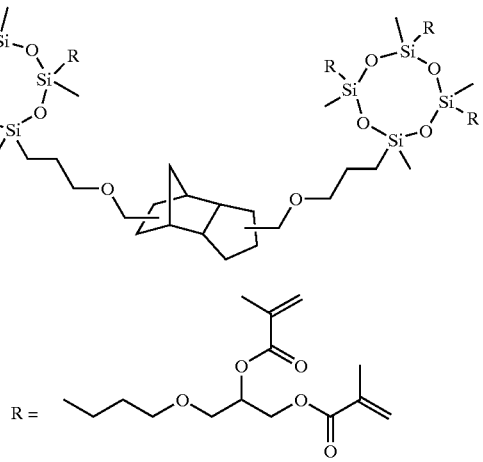

n = 1, A = methyl, B = tricyclo[5.2.1.0$^{2,6}$]decane-diyl, G = 1,3-propanediyl,
Q = glycerol-triyl, L = methacryl.

Those compounds which wholly or partly bear acryl, instead of methacryl, groups are also particularly preferred.

It was also found that compounds of the following general formula (II) can also achieve the object described above $$V-O-\left[\begin{array}{c}T\\|\\Si\\|\\T\end{array}-O\right]_b\left[\begin{array}{c}T\\|\\Si\\|\\N\end{array}-O\right]_c-V \quad (II)$$

in which:
T=independently of each other H or $C_1$–$C_{10}$ alk(en)yl, preferably methyl, ethyl, propyl, butyl, vinyl, ethinyl, allyl, $C_3$–$C_{10}$ cycloalk(en)yl, preferably cyclopentyl, cyclohexyl, cyclopentadienyl, cyclohexenyl, $C_6$–$C_{12}$ aryl, preferably phenyl, tolyl, xylyl, or $C_8$–$C_{18}$ alkaryl, preferably phenylethylenyl;
N=a polymerizable group $R^1$—$R^2$—$R^3$;
b=0 to 500, preferably 0 to 100, where the proportion b may be at most 50% of the repeat units (b+c), but preferably 25% or less;
c=1 to 1000, preferably 1 to 500;
$R^1$=$C_1$–$C_{10}$ alk(en)ylene, preferably ethylene, methylethylene, propylene, butylene, hexylene, ethenylene, propenylene;
$R^2$=O, N—T or a di- or polyvalent linear, branched or cyclic alcohol, amine or aminoalcohol radical with 2 to 10 C atoms, preferably ethanediol-diyl, glycerol-triyl, trimethylolpropane-triyl, pentaerythritol-tetryl;
$R^3$=an organic radical, containing a C=C double bond, with 3 to 10 C atoms, preferably acryl or methacryl;
V=SiMe$_2$T, SiEt$_2$T, SiMePhT, SiPh$_2$T.

Substances according to formula (II) are known and the synthesis of some exemplary representatives is described for example in B. Marciniel: Appl. Organomet. Chem. (1997), 11, 843–849. Their suitability for use in dental compositions has not however been hitherto disclosed.

The functionalized siloxane monomers of formulae (I) and (II) can each be used either alone, as a mixture with one another or with the addition of customary monomers.

Co-monomers are at least singly ethylenically unsaturated. Preferably used ethylenically unsaturated co-monomers are acrylates or methacrylates. Suitable are generally mono- and polyfunctional (meth)acrylate monomers. Typical representatives of this class of compounds (DE-A-43 28 960) are alkyl(meth)acrylates, including the cycloalkyl(meth)acrylates, aralkyl(meth)acrylates and 2-hydroxyalkyl-(meth)acrylates, for example hydroxypropyl methacrylate, hydroxyethyl methacrylate, isobornyl acrylate, isobornyl methacrylate, butyl glycol methacrylate, acetyl glycol methacrylate, triethylene glycol dimethacrylate, polyethylene glycol dimethacrylate, 2-phenyl-ethyl methacrylate, 2-ethylhexyl methacrylate, cyclohexyl methacrylate, lauryl methacrylate and hexanedioldi(meth)acrylate. Long-chained monomers of U.S. Pat. No. 3,066,112 based on Bisphenol A and glycidyl methacrylate or their derivatives resulting from addition of isocyanates can also be used. Also suitable are compounds of the type Bisphenyl-A-diethyloxy(meth)acrylate and Bisphenol-A-dipropyloxy(meth)acrylate. The oligoethoxylated and oligopropoxylated Bisphenol-A dicacrylic and dimethacrylic acid esters can also be used. Also well suited are the diacrylic and dimethacrylic acid esters of Bis(hydroxy-methyl)tricyclo[5.2.1.0$^{2,6}$]decane named in DE-C-28 16 823 and the diacrylic and dimethacrylic acid esters of the compounds of Bis(hydroxymethyl)-tricyclo[5.2.1.0$^{2,6}$]-decane extended with 1 to 3 ethylene oxide and/or propylene oxide units.

The dental compositions according to the invention contain the following components:
i) 0 to 70, preferably 5 to 15 parts by mass monomers according to formula (I),
ii) 0 to 70, preferably 5 to 15 parts by mass monomers according to formula (II),
iii) 0 to 50, preferably 3 to 10 parts by mass co-monomers,
iv) 20 to 90, preferably 70 to 85 parts by mass fillers,
v) 0.001 to 5, preferably 0.1 to 2 parts by mass initiators,
vi) 0 to 20 parts by mass auxiliaries,
with the proviso that either component i) and/or component ii) is included at the rate of at least 5 parts by mass.

The fillers of the compositions disclosed here (component (iv) are as a rule inorganic fillers. There may be cited by way of example quartz, ground glasses, silica gels as well as pyrogenic silicic acids and precipitation silicic acids or their granules. X-ray-opaque fillers are also preferably used, at least partially. These can for example be X-ray-opaque glasses, that is to say glasses which for example contain strontium, barium or lanthanum (e.g. according to U.S. Pat. No. 3,971,754) or a part of the fillers consists of an X-ray-opaque additive, such as for example yttrium trifluoride, strontium hexafluorozirconate or fluorides of the rare earth metals (e.g. according to EP-A-0 238 025). For better incorporation in the polymer matrix, it is of advantage to hydrophobize the inorganic fillers. Customary hydrophibization agents are silanes, for example trimethoxymethacryloyloxypropyl silane or trimethoxyglycidyl silane.

The fillers preferably have an average grain size <20 µm and in particular <5 µm and an upper grain limit of 150, preferably 70 µm and in particular 25 µm. Particularly preferably, mixtures of 5 to 25% wt.-% fillers with an average grain size of 0.02 to 0.06 µm and 65 to 85% filler with an average grain size of 1 to 5 µm are used.

Systems which are able to form radicals in a suitable period of time are used as initiators (component (v)) of the compositions according to the invention.

In the case of single-component compositions, photoinitiators which can trigger the polymerization reaction through irradiation with UV or visible light are used for this.

Representatives of such photoinitiators are for example benzoin alkyl ethers, benzil ketals, acylphosphinic oxides or aliphatic and aromatic 1,2-diketone compounds, for example camphorquinone, the light polymerization being able to be accelerated by the addition of activators, such as tertiary amines or organic phosphites, in a manner known per se.

Suitable initiator systems for the triggering of the polymerization via a redox mechanism are for example the peroxide/amine or peroxide/barbituric acid derivatives systems and the like. When using such initiator systems it is expedient to keep an initiator (e.g. peroxide) and a catalyst component (e.g. amine) ready separately. The two components are then homogeneously mixed with each other shortly before they are used.

Suitable auxiliaries as per component (vi) may for example be stabilizers, pigments or diluents customarily used in the dental field.

The preparation process of the compositions disclosed here is preferably such that the liquid constituents are mixed with one another, the initiators, if they are not liquid, are dissolved therein by stirring and the filling substances are then added and well homogenized by kneading.

Two-component preparations which are cured by redox mechanisms are formulated such that the essential constituents of the redox initiation system are each introduced separately into a part of the two-component preparation. The distribution of the constituents of the overall preparation is based on the relevant storage properties and the desired mixing ratio.

The polymerizable compositions are characterized by a high filler content and associated high strength, while simultaneously displaying good processability.

The compositions according to the invention are suitable in particular as materials for dental purposes, for example for the production of artificial teeth or temporary fittings, as coating products, for the gluing of substrates and as dental filling materials.

The invention is explained in more detail in the following by means of examples.

PREPARATION EXAMPLE

Preparation of 1,3,5,7 tetramethyl-1,3,5,7-tetrakis-(3-methacryloxypropyl)-cyclotetrasiloxane 3.6 g 1,3,5,7-tetramethylcyclotetrasiloxane, 38.2 g allyl methacrylate and 110 ml toluene are stirred with Karstedt catalyst (3–3.5% Pt, 300 ppm Pt, ABCR) for 24 hours. The reaction is checked by means of IR, the mixture stirred further while the Si—H band is still present at approximately 2100 cm$^{-1}$ and the solvent is then removed under vacuum.

Yield 46.7 g=90%.

Application Examples 1–6, Comparison Example

Preparation of dental compositions with and without use of the monomers of type (I) and (II)

The tetrakismethacrylcyclotetrasiloxane prepared according to the preparation example was used for the preparation of the dental preparations according to the invention. This component was omitted for the comparison example.

The pasty preparations according to the application examples 1 to 6 and according to the comparison example, the compositions of which are described in Table 1, were prepared in a 100-ml laboratory kneader.

The compressive and bending strengths and the E-modulus of the preparations were characterized according to DIN ISO 4049.

The testpieces were prepared by 40 seconds' irradiation of the pasty preparations introduced into moulds using the Elipar II light apparatus from ESPE Dental AG, Germany.

Following removal from the mould, the testpieces were stored in deionized water at 36° C. for a period of 24 hours, after which the mechanical properties were ascertained.

The volume shrinkage occurring during the radical polymerization was established by measuring the densities of the pasty preparations and of the cured compositions, using the buoyancy method.

Table 2 contains a summary of the property values ascertained for the cured preparations according to the application examples 1 to 6 and according to the comparison example.

TABLE 1

Composition of the pasty preparations according to the application examples 1 to 6 and the comparison example

| | Proportions in wt. - % | | | | | | |
|---|---|---|---|---|---|---|---|
| | Application example no. | | | | | | |
| Constituent | 1 | 2 | 3 | 4 | 5 | 6 | Comparison ex. |
| 1,3,5,7-tetramethyl-1,3,5,7-tetrakis-(3-methacryloxypropyl)cyclotetrasiloxane | 9.60 | 5.11 | 13.40 | 8.32 | 16.30 | 7.80 | — |
| Quartz powder, average particle size 1.5 micrometers, silanized | 78.10 | | 80.10 | 77.30 | 70.70 | 30.72 | 41.30 |

TABLE 1-continued

Composition of the pasty preparations according to the application examples 1 to 6 and the comparison example

| | Proportions in wt. - % | | | | | | |
|---|---|---|---|---|---|---|---|
| | Application example no. | | | | | | |
| Constituent | 1 | 2 | 3 | 4 | 5 | 6 | Comparison ex. |
| Strontium silicate glass, average particle size 1.2 micrometers, silanized | | 75.30 | | | 8.20 | 47.11 | 35.01 |
| 2,2-bis-4(3-hydroxypropoxyphenyl)-propane-dimethacrylate | | 4.89 | | | 4.46 | | 7.55 |
| 2,2-bis-4(2-hydroxypropoxyphenyl)-propane dimethacrylate | | | | | | 3.77 | |
| 7,7,9-trimethyl-4,13-dioxo-3,14-dioxa-5,12-diaza-hexadecane-1,16-dioldimethacrylate | 11.82 | | 6.13 | 7.30 | | | |
| Bis-acryloyloxymethyltricyclo[5.2.1.0$^{2,6}$]-decane | | 14.27 | | 6.70 | | 10.24 | 15.73 |
| 2,2'-(3-methoxypropylnitrilo)diethanoldimethacrylate | 0.41 | 0.37 | 0.30 | 0.30 | 0.27 | 0.29 | 0.35 |
| 1,7,7-trimethyl-bicyclo-[2,2,1]-heptanedion-2,3 | 0.07 | 0.06 | 0.07 | 0.08 | 0.07 | 0.07 | 0.06 |

TABLE 2

Summary of the property values, ascertained for the cured preparations according to the application examples 1 to 6 and the comparison example

| | Application examples no. | | | | | | |
|---|---|---|---|---|---|---|---|
| Property | 1 | 2 | 3 | 4 | 5 | 6 | Comparison example |
| Compressive strength/Mpa | 416 | 407 | 437 | 447 | 426 | 398 | 411 |
| Bending strength/Mpa DIN ISO 4049 | 97 | 112 | 119 | 104 | 115 | 118 | 117 |
| Elasticity modulus/Mpa | 7348 | 7150 | 8731 | 8121 | 8713 | 8050 | 8120 |
| Volume shrinkage/% using the buoyancy method | 2.81 | 3.19 | 2.73 | 3.08 | 2.67 | 3.27 | 3.67 |

What is claimed is:

1. A cyclic siloxane compound of the following general formula (I):

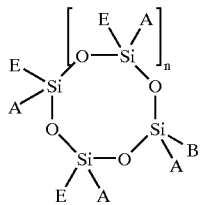

in which:

n=0, 1, 2, 3, 4, 5, 6, 7, 8, 9, 10;

A=H or $C_1$–$C_{15}$ alk(en)yl, $C_3$–$C_{15}$ cycloalk(en)yl, $C_6$–$C_{12}$ aryl, $C_8$–$C_{18}$ alkaryl, where, in the said radicals, in each case one or more C atoms can be replaced by O, C=O, O(C=O), $SiR_2$ and/or NR, R being an aliphatic radical with 1 to 7 C atoms, in which one or more C atoms can be replaced by O, C=O, and/or O(C=);

B=E or a linear, branched or polycyclic aliphatic- or aromatic-groups-containing hydrocarbon radical which links 2 to 10 of the cyclosiloxane radicals defined above, less B, to one another and contains 2 to 50C atoms and additionally 0 to 30 other atoms from the group O, N, S, P, Si, Cl, F, Br, I and from which correspondingly 1 to 9 of the above defined cyclosiloxane radicals, less B, are pending;

E=A or a polymerizable group G—Q—L, where on average up to 25% or less of the groups E correspond to representatives of A;

G=$C_{1-10}$ alk(en)ylene;

Q=O, N—A or a di-or polyvalent linear, branched or cyclic alcohol, amine or aminoalcohol radical with 2 to 10 C atoms;

L=an organic radical, containing a C=C double bond, with 2 to 10 C atoms;

and with the proviso that no annelated siloxane ring systems can occur in (I).

2. A dental composition containing i) 5 to 70 parts by mass monomers according to formula (I), ii) 0 to 15 parts by mass monomers according to formula (II), iii) 0 to 50 parts by mass co-monomers, iv) 20 to 90 parts by mass fillers, v) 0.001–5 parts by mass initiators, vi) 0 to 20 parts by mass auxiliaries, where component I) are compounds of the following general formula (I):

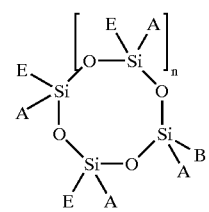

in which:

n=0, 1, 2, 3, 4, 5, 6, 7, 8, 9, 10;

A=H or $C_1$–$C_{15}$ alk(en)yl, $C_3$–$C_{15}$ cycloalk(en)yl, $C_6$–$C_{12}$ aryl, $C_8$–$C_{18}$ alkaryl, where, in the said radicals, in each case one or more C atoms can be replaced by O, C=O, O(C=O), $SiR_2$ and/or NR, R being an aliphatic radical with 1 to 7 C atoms, in which one or more C atoms can be replaced by O, C=O, and/or O(C=);

B=E or a linear, branched or polycyclic aliphatic- or aromatic-groups-containing hydrocarbon radical which links 2 to 10 of the cyclosiloxane radicals defined above, less B, to one another and contains 2 to 50C atoms and additionally 0 to 30 other atoms from the group O, N, S, P, Si, Cl, F, Br, I and from which correspondingly 1 to 9 of the above defined cyclosiloxane radicals, less B, are pending;

E=A or a polymerizable group G—Q—L, where on average up to 25% or less of the groups E correspond to representatives of A;

G=$C_{1-10}$ alk(en)ylene;

Q=O, N—A or a di-or polyvalent linear, branched or cyclic alcohol, amine or aminoalcohol radical with 2 to 10 C atoms;

L=an organic radical, containing a C=C double bond, with 2 to 10 C atoms;

and with the proviso that no annelated siloxane ring systems can occur in (I)

and where component ii) are compounds of the following general formula (II):

$$V-O\left[\begin{array}{c}T\\|\\Si\\|\\T\end{array}-O\right]_b\left[\begin{array}{c}T\\|\\Si\\|\\N\end{array}-O\right]_c V \quad (II)$$

in which:

T=independently of each other H or $C_1$–$C_{10}$ alk(en)yl, $C_3$–$C_{10}$ cycloalk(en)yl, $C_6$–$C_{12}$ aryl or $C_8$–$C_{18}$ alkaryl;

N=a polymerizable group $R^1$—$R^2$—$R^3$;

b=0 to 500, where the proportion b may be at most 50% of the repeat units (b+c);

c=1 to 1000;

$R^1$=$C_1$–$C_{10}$ alk(en)ylene;

$R^2$=O, N—T or a di- or polyvalent linear, branched or cyclic alcohol, amine or aminoalcohol radical with 2 to 10 C atoms;

$R^3$=an organic radical, containing a C=C double bond, with 3 to 10 C atoms;

V=$SiMe_2T$, $SiEt_2T$, $SiMePhT$, $SiPh_2T$.

3. The dental composition according to claim 2, in which the variables of the compounds (II) are defined as follows:

T=methyl, ethyl, propyl, butyl, vinyl, ethinyl, allyl, cyclopentyl, cyclohexyl, cyclopentadienyl, cyclohexenyl, phenyl, tolyl, xylyl, phenylethylenyl;

b=0 to 100, whereby the proportion b may be 25% or less of the repeat units (b+c);

c=1 to 500;

$R^1$=ethylene, methylethylene, propylene, butylenes, hexylene, ethenylene, propenylene;

$R^2$=ethanediol-diyl, glycerol-triyl, trimethylolpropane-triyl, pentaerythritol-tetryl;

$R^3$=acryl or methacryl.

4. A method for the preparation of polymerizable filling materials, fixing cements, inlays, onlays, facing shells and temporary crowns and bridge compositions which comprises the step of formulating a pasty preparation comprising the composition of claim 2.

5. The method of preparing the dental composition according to claim 2, which comprises the step of mixing the components (i) and (ii), optionally (iii), (iv), (v) and optionally (vi) with one another.

6. The cyclic siloxane compound of claim 1 in which n is 1, 2, 3, 4, 5 and wherein, in the definition of B, 1 to 4 of the cyclosiloxane radicals, less B, are pending.

7. The dental composition of claim 2 in which n is 1, 2, 3, 4, 5 and wherein, in the definition of B, 1 to 4 of the cyclosiloxane radicals, less B, are pending.

* * * * *

UNITED STATES PATENT AND TRADEMARK OFFICE
CERTIFICATE OF CORRECTION

PATENT NO. : 6,566,413 B1
DATED : May 20, 2003
INVENTOR(S) : Weinmann, Wolfgang

It is certified that error appears in the above-identified patent and that said Letters Patent is hereby corrected as shown below:

Title page,
Item [57], ABSTRACT,
Line 32 (excluding figure), delete "$C_8$-$C_8$" and insert -- $C_8$-$C_{18}$ --, therefor.

Column 2,
Line 42, delete "16-hexanediol" and insert -- 1,6-hexanediol --, therefore.

Column 8,
Line 1, (excluding figure), delete "ethanediol-diyl," and insert -- glycerol-triyl, --, therefor.

Columns 7-8,
Line 4, (excluding figure), delete " 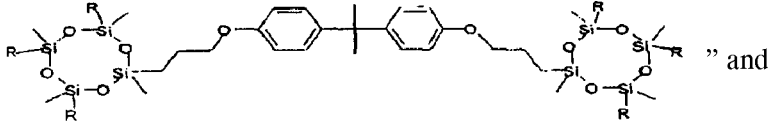 " and insert -- )propane --, therefor.

Columns 9-10,
Figure 2, delete " 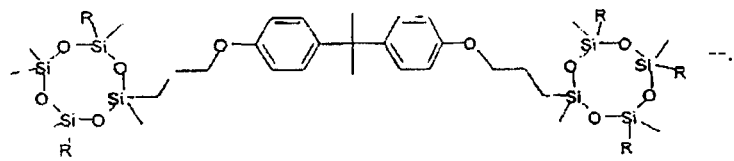 " and insert therefor -- --.

Column 11,
Line 2, (excluding figure), delete ")-propane" and insert -- ) propane --, therefor.
Line 3, (excluding figure), delete ")propane" and insert -- ) propane --, therefor.

Column 13,
Lines 1, 2 and 3, (excluding figure), delete "tr iyl,G" and insert -- triyl, G --, therefor.

UNITED STATES PATENT AND TRADEMARK OFFICE
CERTIFICATE OF CORRECTION

PATENT NO. : 6,566,413 B1
DATED : May 20, 2003
INVENTOR(S) : Weinmann, Wolfgang

It is certified that error appears in the above-identified patent and that said Letters Patent is hereby corrected as shown below:

<u>Columns 15-16,</u>
Lines 1 and 2, (excluding figure), delete "tr iyl,G" and insert -- triyl, G --, therefor.
Line 1, (excluding figure), delete "propanediyl," and insert -- propenediyl, --, therefor.

<u>Columns 23-24,</u>
Table 1, row 5 (excluding heading), after "propane" insert -- - --.

<u>Column 24,</u>
Line 54, delete "I)" and insert -- i) --, therefor.

Signed and Sealed this

Thirteenth Day of September, 2005

JON W. DUDAS
*Director of the United States Patent and Trademark Office*